United States Patent [19]
Adachi et al.

[11] Patent Number: 5,939,360
[45] Date of Patent: Aug. 17, 1999

[54] COMPOUND AND HERBICIDAL COMPOSITION FOR WEED CONTROL

[75] Inventors: Hiroyuki Adachi, Kanagawa; Masao Yamaguchi, Hiratsuka; Masami Koguchi, Odawara; Akihiro Takahashi, Ohi-machi; Takashi Kawana, Minamiashigara; Katsunori Tanaka; Osamu Miyahara, both of Odawara, all of Japan

[73] Assignee: Nippon Soda Co., Ltd., Tokyo, Japan

[21] Appl. No.: 09/212,794

[22] Filed: Dec. 15, 1998

Related U.S. Application Data

[63] Continuation-in-part of application No. 08/875,581, Jul. 8, 1997.

[51] Int. Cl.[6] .......................... A01N 43/80; C07D 413/10
[52] U.S. Cl. ............................................. 504/271; 548/247
[58] Field of Search .............................. 548/247; 504/271

[56] References Cited

FOREIGN PATENT DOCUMENTS

| | | |
|---|---|---|
| 2-000173 | 1/1990 | Japan . |
| 93/18031 | 9/1993 | WIPO . |
| 96/26206 | 8/1996 | WIPO . |

*Primary Examiner*—Laura L. Stockton
*Attorney, Agent, or Firm*—Joseph C. Mason, Jr.; Dennis G. LaPointe

[57] ABSTRACT

The present invention is directed to a compound of formula [I]:

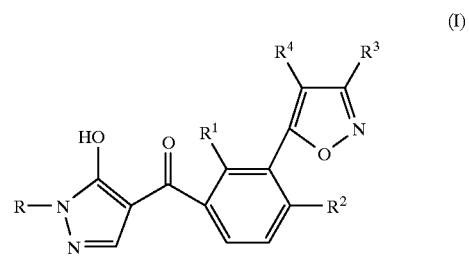

or a salt thereof in which $R_1$ is a a $C_{1-6}$ alkyl group, $R^2$ is a halogen atom, a $C_{1-6}$ alkylthio group, a $C_{1-6}$ alkylsulfinyl group or a $C_{1-6}$ alkylsulfonyl group, $R^3$ and $R^4$ are each independently hydrogen, a $C_{1-6}$ alkyl group or a $C_{1-6}$ haloalkyl group, and R is hydrogen or a $C_{1-6}$ alkyl group. The present invention is further directed to a compound of formula [1] or a salt thereof, as described above and in which $R^1$ and $R^3$ are methyl, $R^2$ is chlorine or methylsulfonyl, $R^4$ is hydrogen, and R is methyl or ethyl. In addition, the present invention is directed to a herbicidal composition, characterized in that it contains as active agent one or more compounds of formula [I] or salt thereof in which $R^1$, $R^2$, $R^3$, $R^4$ are as described above.

4 Claims, No Drawings

COMPOUND AND HERBICIDAL COMPOSITION FOR WEED CONTROL

RELATED APPLICATION

This application is a continuation-in-part of U.S. patent application Ser. No. 08/875,581 filed Jul. 8, 1997.

FIELD OF THE INVENTION

The present invention relates to a novel pyrazole derivative substituted by a benzoyl group at the at the 4-position of a pyrazole ring, and a herbicide.

1. Background Art

In WO 93/18031 Gazette, a compound of formula [II];

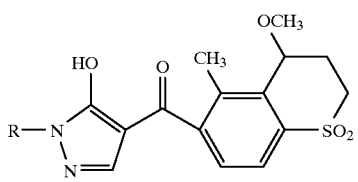

[II]

is disclosed as an active component of a herbicide having a pyrazole skeltone substituted by a benzoyl group at the 4-position of its pyrazole ring.

On the other hand, in WO 96/26206 Gazette, a compound of formula [III];

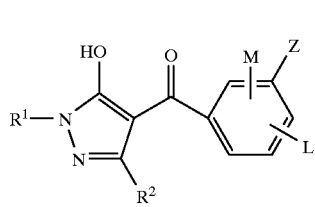

[III]

is disclosed.

2. Disclosure of the Invention

It is an object of the present invention to provide a herbicide which can be advantageously synthesized on an industrial scale, which is firmly effective with a lower dosage thereof and is highly safe, and which has a higher selectivity in its herbicidal activity between weeds and crops. The present invention is directed to a herbicide which contains, as an effective component, a 4-benzoylpyrazole compound, structurally characterized in that the 3-position of a benzoyl moiety represented by a general formula [I] is substituted by a heterocycle, and a substituent at the 2-position is a $C_{1-6}$ alkyl group.

That is to say, the present invention is directed to a compound of formula [I] or a salt thereof;

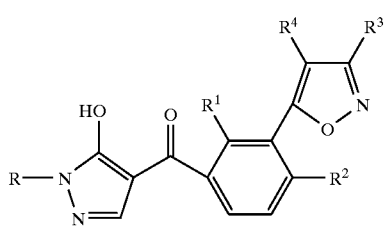

[I]

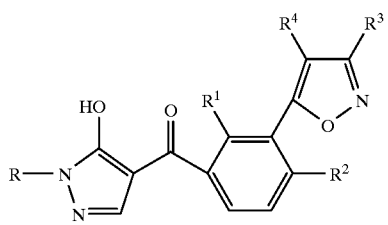

[I]

wherein $R^1$ is a $C_{1-6}$ alkyl group, $R^2$ is a halogen atom, a $C_{1-6}$ alkylthio group a $C_{1-6}$ alkylsulfinyl group or a $C_{1-6}$ alkylsulfonyl group, $R^3$ and $R^4$ are each independently hydrogen, a $C_{1-6}$ alkyl group or a $C_{1-6}$ haloalkyl group, and R is a hydrogen atom or $C_{1-6}$ alkyl group, and a herbicidal composition comprising such compound or such salt.

Now, the present invention is described in detail in the following.

The present invention is directed to a pyrazole compound of formula [I];

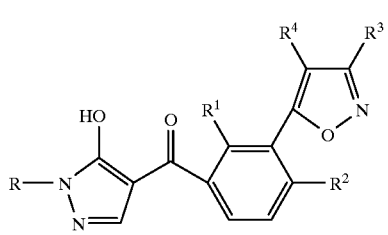

[I]

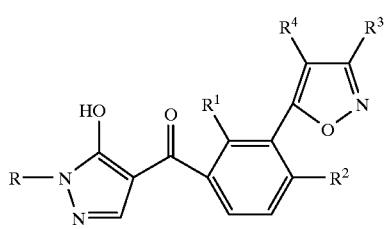

[I]

and a herbicidal composition comprising said compound as the active component.

In formula [I], $R^1$ is a $C_{1-6}$ alkyl group, such as methyl, ethyl, propyl, isopropyl. butyl and t-butyl.

$R^2$ is a halogen atom, such as fluorine, chlorine ad bromine, a $C_{1-6}$ alkylthio group, such as methylthio, ethylthio, propylthio and isopropylthio, a $C_{1-6}$ alkylsulfinyl group, such as methylsulfinyl, ethylsulfinyl, propylsulfinyl and isopropylsulfinyl, or a $C_{1-6}$ alkylsulfonyl group, such as methylsulfonyl, ethylsulfonyl, propylsulfonyl and isopropylsulfonyl.

$R^3$ and $R^4$ are each independently hydrogen, a $C_{1-6}$ alkyl group, such as methyl, ethyl, propyl, isopropyl, butyl and t-butyl, or a $C_{1-6}$ haloalkyl group, such as trifluoromethyl and trifuloroethyl.

R is hydrogen or a $C_{1-6}$ alkyl group, such as methyl, ethyl, propyl, isopropyl, butyl, isobutyl and t-butyl.

Manufacturing of Compounds

The compounds according to the present invention can be prepared pursuant to the following reaction process.

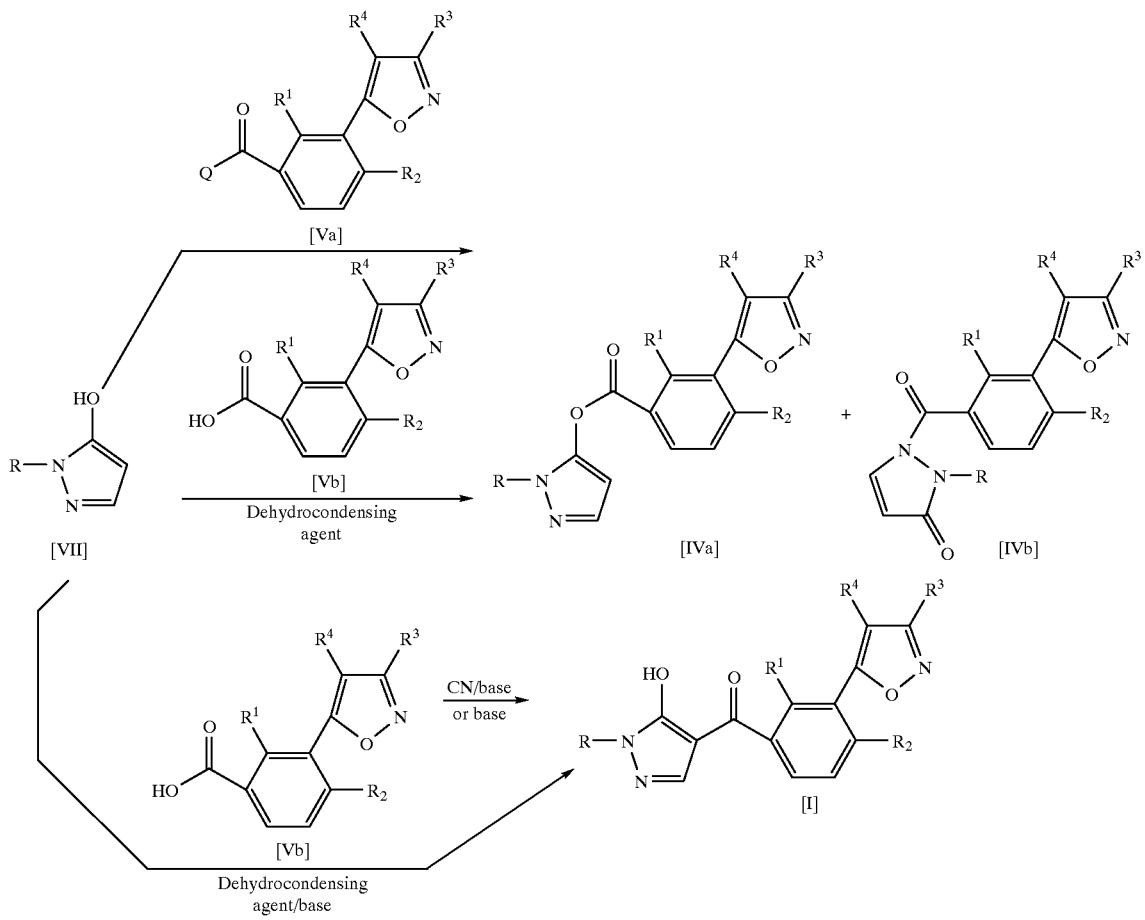

wherein $R^1$, $R^2$, $R^3$, $R^4$ and R are as defined above, and Q is a halogen atom, an alkylcarbonyloxy group, an alkoxycarbonyloxy group or a benzoyloxy group.

In the process illustrated above, compounds of formulas [IVa] and [IVb] can be respectively obtained by reacting a compound of formula [VII] in an amount of 1 mol with a compound of formula [Va] in an amount of 1 mol, wherein Q is as defined above, provided that an excessive amount either of the compound of formula [VII] or the compound of formula [Va] may be used in the said reaction, in the presence of a base either in an amount of I mol or in an excessive amount.

As an example of the base which can be used in the reaction described above, an alkali metal hydroxide, such as KOH and NaOH, an alkali metal carbonate, such as sodium carbonate and potassium carbonate, an alkali earth metal hydroxide, such as calcium hydroxide and magnesium hydroxide, an alkali earth metal carbonate, such as calcium carbonate, a tri($C_{1-6}$ alkyl)amine, such as triethylamine and diisopropylethylamine, an organic base, such as pyridine, and sodium phosphate, etc. can be given.

Furthermore, as an example of the solvent to be used in the reaction described above, water, methylene chloride, chloroform, toluene, ethyl acetate, dimethylformamide (DMF), tetrahydrofuran (THF), dimethoxy ethane (DME), acetonitrile and the like can be given.

The mixture prepared for the reaction described above is stirred at a temperature range of from 0° C. to a boiling point of the solvent used for a duration until completing the said reaction. In addition, the reaction can be carried out in a two-phase system while using a phase-transfer catalyst, such as a quaternary ammonium salt.

Furthermore, the compounds of formulas [IVa] and [IVb] can also be obtained by reacting the compound of formula [VII] and a compound of formula [Vb] in the presence of a dehydrocondensing agent, such as dicyclohexylcarbodimide (DCC). Examples of the solvent which can be used in the reaction with DCC or the like include methylene chloride, chloroform, toluene, ethyl acetate, DMF, THF, dimethoxy ethane, acetonitrile and t-amylalcohol. The reaction mixture is stirred at a temperature range of from −10° C. to a boiling point of the solvent used until completing the reaction. The reaction mixture can be treated pursuant to a customary method.

The compounds of formulas [IVa] and [IVb] are used as a mixture in the following transition reaction. The transition reaction can be carried out in the presence of a cyano compound and a mild base. That is to say, the compound of formula [I] can be obtained by reacting a mixture of the compounds of formulas [IVa] and [IVb] in an amount of 1 mol with a base in an amount of 1 to 4 mol, preferably 1 to 2 mol and a cyano compound in an amount of 0.01 to 1.0 mol, preferably 0.05 to 0.2 mol. As the base which can be used herein, any of the above-mentioned bases can be used. In addition, as examples for the cyano compound, potassium cyanide, sodium cyanide, acetone cyanohydrin, hydrogen cyanide and a polymer containing potassium cyanide are given. If adding a small amount of a phase-transfer catalyst such as crown ether, the reaction can be completed in a shorter period of time. A reaction temperature is less than 80° C., preferably in the range of from room-temperature to 40° C. As examples for the solvent described above. 1,2-dichloro ethane, toluene, acetonitrile, methylene chloride, chloroform, ethyl acetate, DMF, methyl isobutyl ketone, THF and dimethoxy ethane are given.

Furthermore, this transition reaction can also be carried out in a solvent in the presence of a base, such as potassium carbonate, sodium carbonate, triethylamine and pyridine. The amount of the base to be used in the reaction is in a range of from 0.5 to 2.0 mol based on the compounds of formulas [IVa] and [IVb], and as a solvent to be used to the reaction, THF, dioxane, t-amylalcohol and t-butylalcohol can be used. A reaction temperature is in a range of from room temperature to a boiling point of the solvent used.

In addition, a similar transition reaction can also be proceeded by adding a cyano compound and a base as -continued

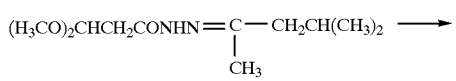

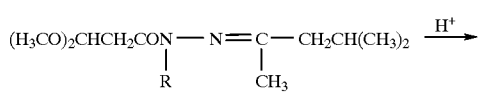

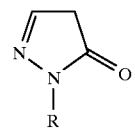

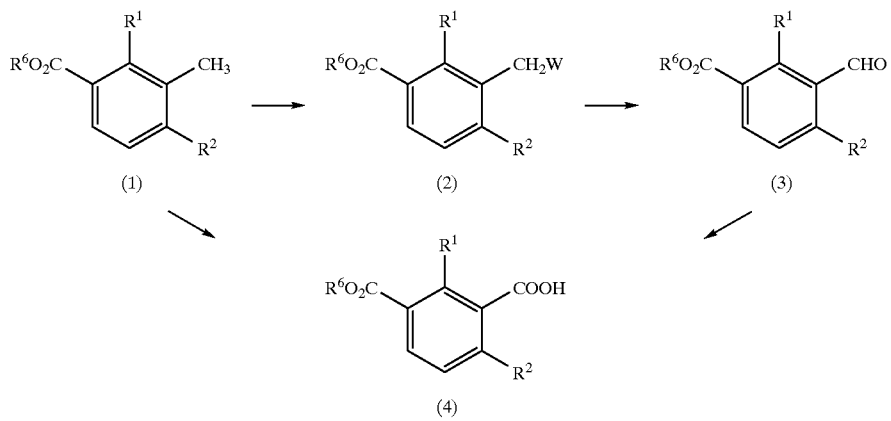

wherein $R^1$ and $R^2$ are as defined above, $R^6$ is hydrogen or a lower alkyl group, and W is a halogen atom.

The aldehyde compound of formula (3) can be prepared from a toluene derivative of formula (1) according to a known method, for example, a method to subject with either of a single halogene substance such as chlorine and bromine, or a halogenating agent, such as N-bromosuccinimide (NBS) and N-chlorosuccinimide (NCS) in the presence of light or a radical reaction initiator such as benzoyl peroxide to obtain a benzyl halide derivative of formula (2), then converting it in accordance with a method described in J. Am. Chem. Soc., Vol. 71, p. 1767 (1949) to the aldehyde compound of formula (3). More specifically, the aldehyde compound of formula (3) can be prepared by reacting a benzyl halide derivative of formula (2) with an alkali metal salt of a nitroalkane such as 2-nitropropane in an alcohol solvent, such as methanol and ethanol, at a temperature of from 0° C. to a boiling point of a solvent used.

Next, the carboxylic acid compound of formula (4) can be prepared from a toluene derivative of formula (1) by an oxidation reaction of potassium permanganate or the like, or alternatively it can be prepared from the aldehyde compound of formula (3) according to a known method employing an oxidation reaction with any of Jones reagent, chromic acid, potassium permanganate or the like.

Furthermore, by using both aldehyde compound of formula (3) and carboxylic acid compound of formula (4), intermediates as shown hereinbelow can be prepared.

described above to the reaction mixture without isolating compounds of formulas [IVa] and [IVb].

Furthermore, the compound of formula [I] can also be obtained by using a base together with a dehydrocondensing agent such as DCC without isolating compounds of formulas [IVa] and [IVb]. As examples for the base said above, potassium carbonate, sodium carbonate, triethylamine and pyridine are given. The amount of the base to use is in a range of from 0.5 to 2.0 mol based on the compound of formula [VII]. In addition, as examples for a solvent usable in this reaction, THF, dioxane, t-amylalcohol, t-butylalcohol, etc. are given, and a reaction temperature is in a range of from room temperature to a boiling point of the solvent used.

5-hydroxypyrazole compounds of formula [VII] can be prepared according to the following reaction processes, which are described in Japanese Patent Application Laid-open No. Sho 62-234069 Gazette and Japanese Patent Application Laid-open No. Hei 3-44375 Gazette.

(a)

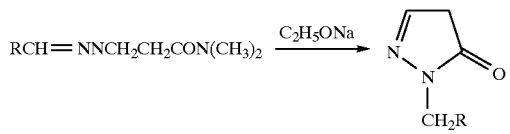

(b)

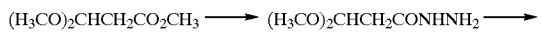

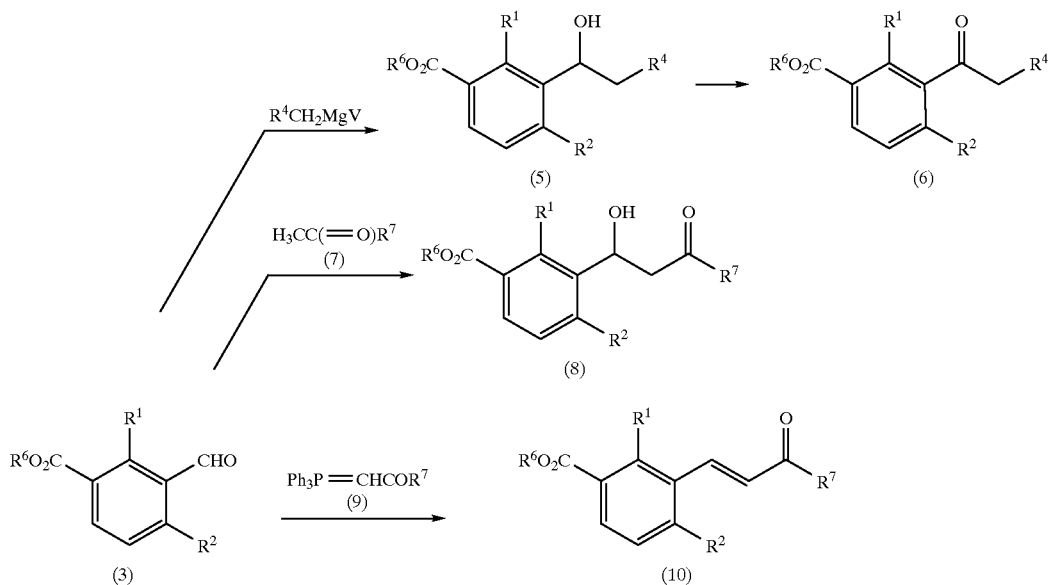

wherein $R^1$, $R^2$ and $R^6$ are as defined above, $R^7$ is a lower alkyl group, and $R^4$ is hydrogen or a lower alkyl group.

A corresponding acyl compound of formula (6) can be obtained by firstly preparing an alcohol compound of formula (5), which can be prepared in a reaction of an aldehyde compound of formula (3) with Grignard reagent, and subsequently oxidizing the alcohol compound of formula (5) with any of activated manganese dioxide, chromic acid and the like.

A vinyl ketone compound of formula (10) can be prepared by reacting the aldehyde compound of formula (3) with a methyl ketone compound of formula (7) in the presence of a catalyst at a temperature of from 0 to 100° C. for 1 to 50 hours in a solvent, such as water, toluene and chloroform, or a mixed solvent consisted of water and toluene, chloroform, etc. to obtain an aldol compound of formula (8), and then dehydrating the aldol compound in the presence of a catalyst in a suitable solvent.

As examples for the catalyst used in the reaction for preparing said aldol compound of formula (8), a metal hydroxide, such as sodium hydroxide and barium hydroxide, and an organic base, such as piperidine and pyridine are given.

Furthermore, as examples for the catalyst which can be used in the dehydration reaction described above, an acid, such as concentrated sulfuric acid and p-toluenesulfonic acid are given. In addition, as examples for the solvent used in said dehydration reaction, a hydrocarbon, such as benzene and toluene, and a halogenated hydrocarbon, such as dichloromethane and chloroform, are given.

The vinyl ketone compound of formula (10) can also be prepared by reacting an aldehyde compound of formula (3) with a phospholane compound of formula (9) in a suitable solvent at a temperature range of from room temperature to a boiling point of a solvent used for a period of 10 minutes to 30 hours.

A β-diketone compound of formula (12) can be prepared according to the following process.

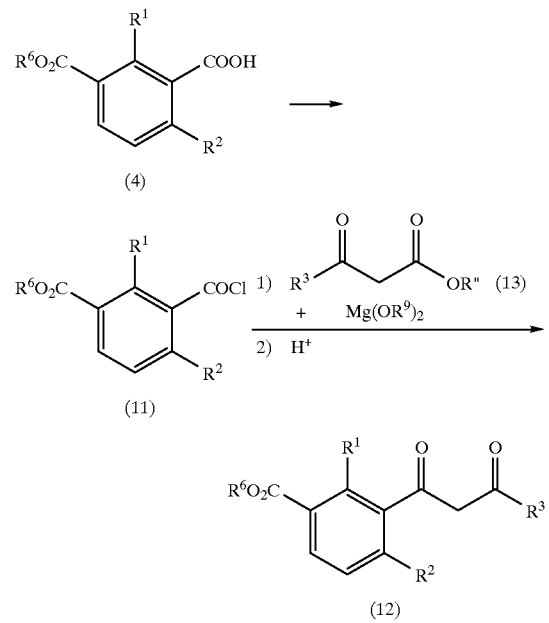

wherein $R^1$, $R^2$, $R^3$ and $R^6$ are as defined above, and R" and $R^9$ are each independently a lower alkyl group.

In the reaction process as shown above, a carboxylic acid compound of formula (4) is reacted with a chlorinating agent, such as phosgene, thionyl chloride and oxalyl chloride, in an inert solvent, such as a hydrocarbon like benzene or toluene and a halogenated hydrocarbon like methylene chloride or chloroform, to prepare a carbonyl chloride compound of formula (11) which is an intermediate.

Then, a β-diketone compound of formula (12) can be prepared by reacting a carbonyl chloride compound of formula (11) with a magnesium salt of a β-ketoester compound (13), which salt can be obtained by subjecting a β-ketoester compound of formula (13) to a reaction with magnesium alcoholate in accordance with a known method.

Now, a method for preparing an isoxazole compound, which is an intermediate, is explained hereinbelow.

Manufacturing Method 1

(Manufacturing Method 1)

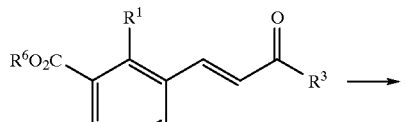

(10)

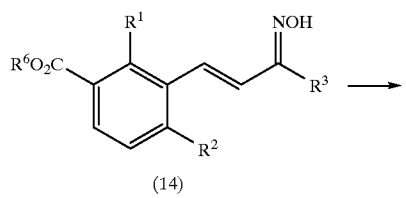

(14)

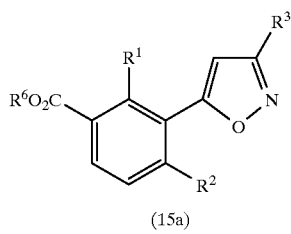

(15a)

In the reaction process shown above, $R^1$, $R^2$, $R^3$ and $R^6$ are as defined above.

An isoxazole compound of formula (15a) can be prepared by firstly reacting a vinyl ketone compound of formula (10) with a hydroxylamine in an appropriate solvent at a temperature range of from 0° C. to a boiling point of a solvent used for a period of 0.5 to 5 hours to obtain an oxime compound of formula (14) and subsequently subjecting the said oxime compound to both ring closing reaction and oxidation reaction. In this oxime formation reaction, either sulfate or hydrochloride of hydroxylamine can be used even without neutralization, however, such hydroxylamine salts may be used after neutralizing them by using an appropriate base.

As examples for the base used in the reaction, a carbonate, such as sodium hydrogencarbonate and potassium carbonate, an alkali metal hydroxide, such as sodium hydroxide and potassium hydroxide, a carboxylate, such as sodium acetate, a metallic alcoholate, such as sodium methylate and sodium ethylate, and an organic base, such as triethylamine and pyridine can be given.

Furthermore, as examples for the solvent used in the reaction, an alcohol, such as methanol, ethanol and isopropanol, a hydrocarbon, such as benzene and toluene, a halogenated hydrocarbon, such as dichloromethane and chloroform, an ether, such as THF and dioxane, a nitrile such as acetonitrile, DMF, pyridine, acetic acid, water, and a mixed solvent consisting of two or more thereof are given.

In the ring closing reaction and the oxidation reaction described above, iodine-potassium iodide, N-bromosuccinimide or a palladium catalyst can be used, and the objective compounds can be prepared in accordance with a method described in J. Amer. Chem. Soc., p. 94 (1972), J. Heterocycl. Chem., Vol. 14, p. 1289 (1977), and Tetrahedron Lett. p. 5075 (1977).

Manufacturing Method 2

(Manufacturing Method 2)

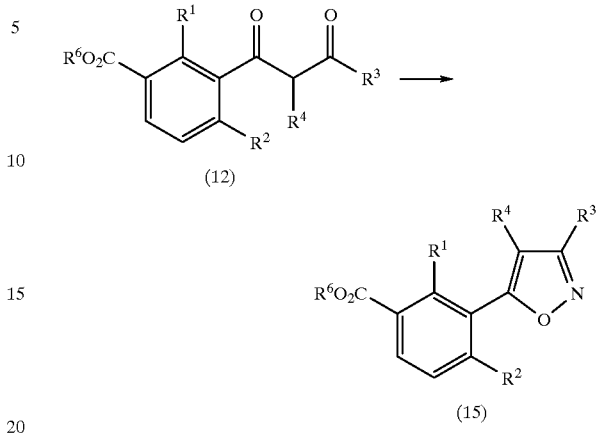

In the process described above, $R^1$, $R^2$, $R^3$, $R^4$ and $R^6$ are as defined above.

An isoxazole compound of formula (15) can also be prepared by reacting a β-diketone compound of formula (12) with either hydroxylamine or a hydroxylamine salt. This reaction can be carried out in an appropriate solvent at a temperature range of from 0° C. to a boiling point of a solvent used. In this reaction, an acid, such as sulfuric acid and p-toluenesulfonic acid, can also be used as a catalyst.

As examples for the solvent used in the reaction, an alcohol, such as methanol, ethanol and isopropanol, a hydrocarbon, such as benzene and toluene, a halogenated hydrocarbon, such as dichloromethane and chloroform, an ether, such as THF and dioxane, a nitrile such as acetonitrile, DMF, pyridine, acetic acid, water, and a mixed solvent consisting of two or more thereof are given.

Manufacturing Method 3

(Manufacturing Method 3)

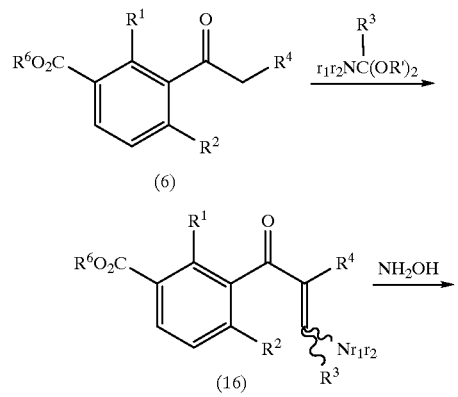

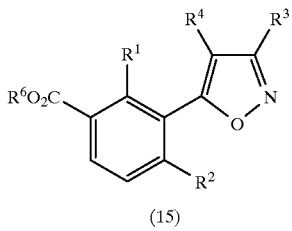

In the reaction process described above, $R^1$, $R^2$, $R^3$, $R^4$ and $R^6$ are as defined above, and $r_1$, $r_2$ and R' represent each independently a lower alkyl group.

Alternatively, the isoxazole compound of formula (15) can be prepared by subjecting a dialkylaminomethylidene compound of formula (16). which is obtained by subjecting the 3-acyl compound of formula (6) described above to a reaction with N,N-dialkylfolmamide dealkylacetal, or N,N dialkylalkylamide diakylacetal, such as N,N-dimethylacetamide dimethylacetal, to either a reaction with either hydroxylamine or a hydroxylamine salt.

Manufacturing Method 4

(Manufacturing Method 4)

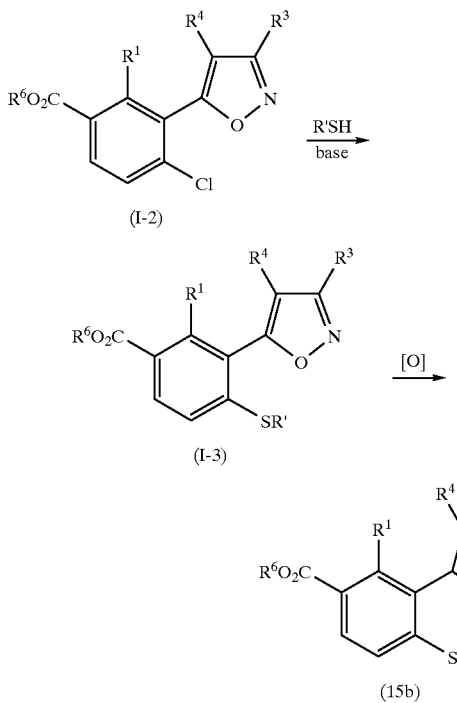

In the reaction process described above, $R^1$, $R^3$, $R^4$ and $R^6$ are as defined above. and R' represents a $C_{1-6}$ alkyl group.

Furthermore, a benzoic acid compound of formula (15b) can be prepared by subjecting a mercapto compound of formula R' SH to a reaction with 4-Cl compound of formula (I-2) in the presence of a base to obtain a 4-SR' compound of formula (I-3) and by subsequently oxidizing the said 4-SR' compound.

As examples for the base used in this reaction, an alkali metal hydroxide, such as sodium hydroxide and potassium hydroxide, a metallic alkoxide, such as sodium methoxide and sodium ethoxide, a carbonate, such as sodium carbonate and potassium carbonate, a hydride such as sodium hydride, and an organic base, such as triethylamine, diisopropylethylamine, 1,8-diaza-bicyclo[5.4.0]-unde-7-cene (DBU) and pyridine, can be given. In addition, as examples for the solvent used in the reaction, an alcohol, such as methanol and ethanol, an ether, such as THF and 1,2-dimethoxyethane (DME), an amide, such as DMF and N,N-dimethylacetamide (DMA), dimethyl sulfoxide (DMSO), acetonitrile, benzene, toluene and xylene can be given. The following oxidation reaction is carried out subject to an use of either an oxidizing agent, for example, a peroxide, such as hydrogen peroxide, peracetic acid, perbenzoic acid and m-chloroperbenzoic acid, or a hypochlorous acid, such as sodium hypochlorite and potassium hypochlorite, in an inert solvent including water, an organic acid, such as acetic acid, and a halogenated hydrocarbon, such as dichloromethane, chloroform and carbon tetrachloride. The reaction can be smoothly proceeded in a temperature range of from room temperature to a boiling point of a solvent used.

Alternatively, a compound of formula (I-3) can be obtained by subjecting a mercapto salt, which is obtained beforehand in a reaction with a mercapto compound of formula, R' SH, and a base, to a reaction with a compound of formula (I-2).

Manufacturing Method 5

In addition, a compound of formula (15) can be prepared according to a method described in WO96/26206 Gazette. The following is a method to prepare said compound of formula (15).

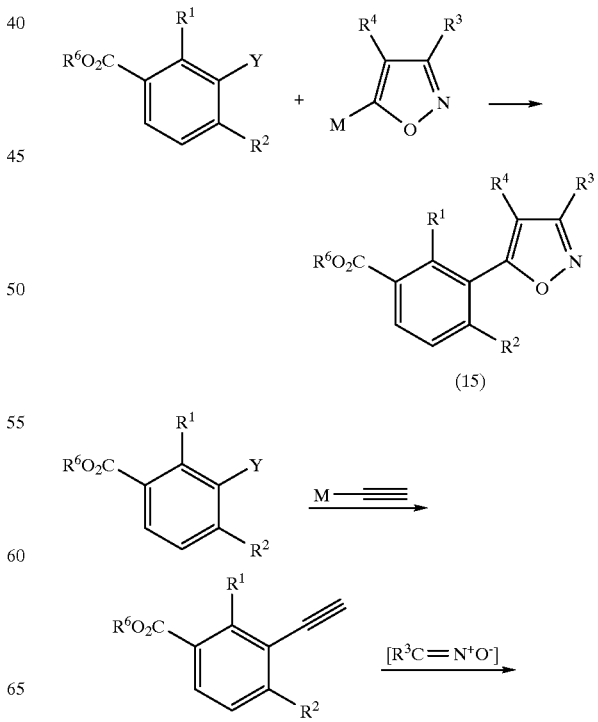

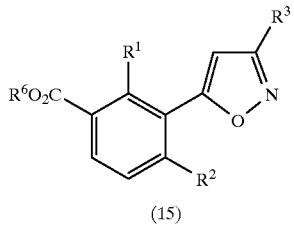

(15)

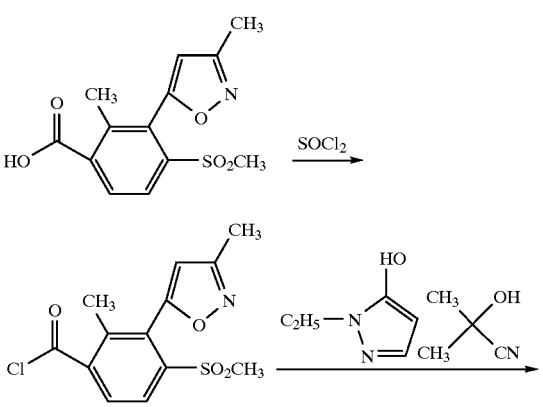

In the reaction process described above, $R^1$, $R^2$, $R^3$ and $R^6$ are as defined above, Y is Br, I, $OSO_2CF_3$, and M is Sn(a $C_{1-6}$ alkyl)$_3$, B(OH.)$_2$ or ZnCl.

Various types of tautomers as illustrated hereinbelow may exist in the compounds of formula [I] according to the present invention. Therefore, it should be noted that all of these tautomers are falling within the scope of the present invention.

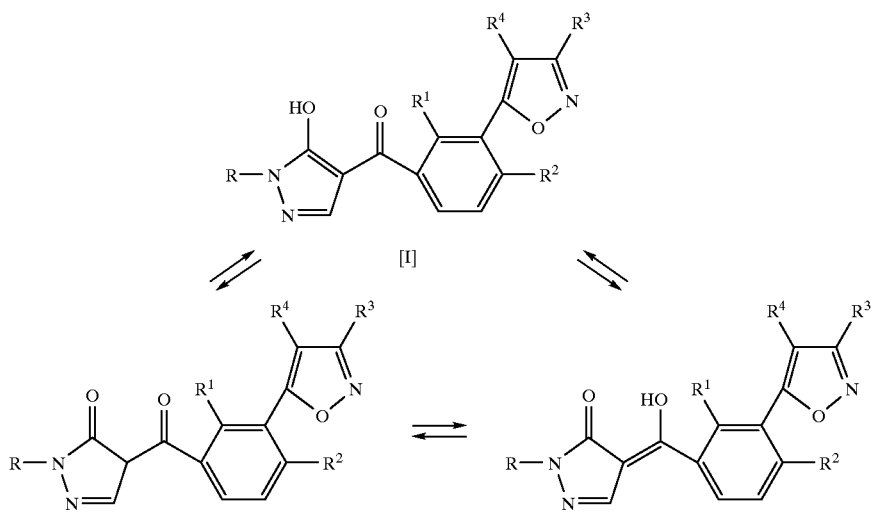

The compounds of the present invention and the various intermediates can be obtained by carrying out pursuant to a customary method for post-treatment following to the completion of reaction.

Structures of the compounds according to the present invention and the various intermediates for manufacturing therefor have been determined by using IR, NMR, MS and other available means.

BEST MODE FOR CARRYING OUT THE INVENTION

Now, the present invention is described in more detail with referring to examples and reference examples described in the following, however, the scope of the present invention should not be limited to the one described in these examples.

Example 1

Preparation of 1-ethyl-5-hydroxy-4-[4-methanesulfonyl-2-methyl-3-(3-methyl-1,2-isoxazol-5-yl)]benzoylpyrazole

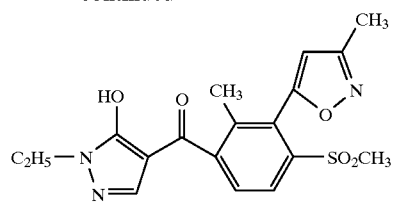

4-methanesulfonyl-2-methyl-3-(3-methyl-1,2-isoxazol-5-yl)benzoic acid in an amount of 1.35 g (4.61 mmol) was dissolved in 15 ml benzene, and 0.71 g (5.97 mmol) of thionyl chloride and one drop of pyridine were added, followed by stirring for 2 hours under heating reflux. After the solution was allowed to cool, the solvent was distilled off under reduced pressure to obtain 1.43 g of 4-methanesulfonyl-2-methyl-3-(3-methyl-1,2-isoxazol-5-yl)benzoyl chloride.

0.38 g (2.6 mmol) of 1-ethyl-5-hydroxypyrazole hydrochloride and 0.51 g (5.1 mmol) of triethylamine were dissolved in 10 ml of methylene chloride, and 2 ml of a methylene chloride solution containing 0.71 g (2.3 mmol) of 4-methanesulfonyl-2-methyl-3-(3-methyl-1,2-isoxazol-5- yl) benzoyl chloride was then added dropwise at room temperature, followed by stirring at room temperature for 1 hour. The resulting reaction mixture was washed with 1N hydrochloric acid and then a saturated sodium chloride solution, and then dried over anhydrous magnesium sulfate, and the solvent was distilled off under reduced pressure. The resulting residue was dissolved in 10 ml of acetonitrile, and 0.47 g (4.7 mmol) of triethylamine and 0.06 g (0.7 mmol) of acetone cyanohydrin were added, followed by stirring at room temperature overnight. The solvent was distilled off under reduced pressure, and the residue was dissolved in ethyl acetate. Afterward, the solution was washed with 1N hydrochloric acid and next a saturated sodium chloride solution, and then dried over anhydrous magnesium sulfate, and the solvent was distilled off under reduced pressure. The remaining crystals were washed with methanol to obtain 0.50 g of the desired compound. m.p.=186 to 189° C.

The representative examples for the compounds according to the present invention prepared as described above are given in Table 1.

TABLE 1

| Compound No. | $R^1$ | $R^2$ | $R^3$ | $R^4$ | R | Melting point (° C.) |
|---|---|---|---|---|---|---|
| 1 | $CH_3$ | Cl | H | H | H | |
| 2 | $CH_3$ | $SO_2CH_3$ | H | H | H | |
| 3 | $CH_3$ | $SO_2C_2H_5$ | H | H | H | |
| 4 | $CH_3$ | Cl | H | H | $CH_3$ | |
| 5 | $CH_3$ | $SO_2CH_3$ | H | H | $CH_3$ | |
| 6 | $CH_3$ | $SO_2C_2H_5$ | H | H | $CH_3$ | |
| 7 | $CH_3$ | Cl | H | H | $C_2H_5$ | |
| 8 | $CH_3$ | $SO_2CH_3$ | H | H | $C_2H_5$ | |
| 9 | $CH_3$ | $SO_2C_2H_5$ | H | H | $C_2H_5$ | |
| 10 | $CH_3$ | Cl | H | H | $i-C_3H_7$ | |
| 11 | $CH_3$ | $SO_2CH_3$ | H | H | $i-C_3H_7$ | |
| 12 | $CH_3$ | $SO_2C_2H_5$ | H | H | $i-C_3H_7$ | |
| 13 | $CH_3$ | Cl | H | H | $t-C_4H_9$ | |
| 14 | $CH_3$ | $SO_2CH_3$ | H | H | $t-C_4H_9$ | |
| 15 | $CH_3$ | $SO_2C_2H_5$ | H | H | $t-C_4H_9$ | |
| 16 | $CH_3$ | Cl | $CH_3$ | H | H | |
| 17 | $CH_3$ | $SO_2CH_3$ | $CH_3$ | H | H | |
| 18 | $CH_3$ | $SO_2C_2H_5$ | $CH_3$ | H | H | |
| 19 | $CH_3$ | Cl | $CH_3$ | H | $CH_3$ | [180–181] |
| 20 | $CH_3$ | $SO_2CH_3$ | $CH_3$ | H | $CH_3$ | [201–204] |
| 21 | $CH_3$ | $SO_2C_2H_5$ | $CH_3$ | H | $CH_3$ | |
| 22 | $CH_3$ | Cl | $CH_3$ | H | $C_2H_5$ | |
| 23 | $CH_3$ | $SO_2CH_3$ | $CH_3$ | H | $C_2H_5$ | [186–189] |
| 24 | $CH_3$ | $SO_2C_2H_5$ | $CH_3$ | H | $C_2H_5$ | |
| 25 | $CH_3$ | Cl | $CH_3$ | H | $i-C_3H_7$ | |
| 26 | $CH_3$ | $SO_2CH_3$ | $CH_3$ | H | $i-C_3H_7$ | |
| 27 | $CH_3$ | $SO_2C_2H_5$ | $CH_3$ | H | $i-C_3H_7$ | |
| 28 | $CH_3$ | Cl | $CH_3$ | H | $t-C_4H_9$ | |
| 29 | $CH_3$ | $SO_2CH_3$ | $CH_3$ | H | $t-C_4H_9$ | |
| 30 | $CH_3$ | $SO_2C_2H_5$ | $CH_3$ | H | $t-C_4H_9$ | |
| 31 | $CH_3$ | Cl | $C_2H_5$ | H | H | |
| 32 | $CH_3$ | $SO_2CH_3$ | $C_2H_5$ | H | H | |
| 33 | $CH_3$ | $SO_2CH_3$ | $i-C_3H_7$ | H | H | |
| 34 | $CH_3$ | $SO_2CH_3$ | $i-C_4H_9$ | H | H | |
| 35 | $CH_3$ | Cl | H | $CH_3$ | H | |
| 36 | $CH_3$ | $SO_2CH_3$ | H | $CH_3$ | H | |
| 37 | $CH_3$ | $SO_2C_2H_5$ | H | $CH_3$ | H | |
| 38 | $CH_3$ | Cl | H | $CH_3$ | $CH_3$ | |
| 39 | $CH_3$ | $SO_2CH_3$ | H | $CH_3$ | $CH_3$ | |
| 40 | $CH_3$ | $SO_2C_2H_5$ | H | $CH_3$ | $CH_3$ | |
| 41 | $CH_3$ | Cl | H | $CH_3$ | $C_2H_5$ | |
| 42 | $CH_3$ | $SO_2CH_3$ | H | $CH_3$ | $C_2H_5$ | |
| 43 | $CH_3$ | $SO_2C_2H_5$ | H | $CH_3$ | $C_2H_5$ | |
| 44 | $CH_3$ | Cl | H | $CH_3$ | $i-C_3H_7$ | |
| 45 | $CH_3$ | $SO_2CH_3$ | H | $CH_3$ | $i-C_3H_7$ | |
| 46 | $CH_3$ | $SO_2C_2H_5$ | H | $CH_3$ | $i-C_3H_7$ | |
| 47 | $CH_3$ | Cl | H | $CH_3$ | $t-C_4H_9$ | |
| 48 | $CH_3$ | $SO_2CH_3$ | H | $CH_3$ | $t-C_4H_9$ | |
| 49 | $CH_3$ | $SO_2C_2H_5$ | H | $CH_3$ | $t-C_4H_9$ | |
| 50 | $CH_3$ | Cl | H | $C_2H_5$ | H | |
| 51 | $CH_3$ | $SO_2CH_3$ | H | $C_2H_5$ | H | |
| 52 | $CH_3$ | $SO_2CH_3$ | H | $i-C_3H_7$ | H | |
| 53 | $CH_3$ | $SO_2CH_3$ | H | $t-C_4H_9$ | H | |
| 54 | $CH_3$ | Cl | $CH_3$ | $CH_3$ | H | |
| 55 | $CH_3$ | $SO_2CH_3$ | $CH_3$ | $CH_3$ | H | |
| 56 | $CH_3$ | $SO_2C_2H_5$ | $CH_3$ | $CH_3$ | H | |
| 57 | $CH_3$ | Cl | $CH_3$ | $CH_3$ | $CH_3$ | |
| 58 | $CH_3$ | $SO_2CH_3$ | $CH_3$ | $CH_3$ | $CH_3$ | |
| 59 | $CH_3$ | $SO_2C_2H_5$ | $CH_3$ | $CH_3$ | $CH_3$ | |
| 60 | $CH_3$ | Cl | $CH_3$ | $CH_3$ | $C_2H_5$ | |
| 61 | $CH_3$ | $SO_2CH_3$ | $CH_3$ | $CH_3$ | $C_2H_5$ | |
| 62 | $CH_3$ | $SO_2C_2H_5$ | $CH_3$ | $CH_3$ | $C_2H_5$ | |
| 63 | $CH_3$ | Cl | $CH_3$ | $CH_3$ | $i-C_3H_7$ | |
| 64 | $CH_3$ | $SO_2CH_3$ | $CH_3$ | $CH_3$ | $i-C_3H_7$ | |
| 65 | $CH_3$ | $SO_2C_2H_5$ | $CH_3$ | $CH_3$ | $i-C_3H_7$ | |
| 66 | $CH_3$ | Cl | $CH_3$ | $CH_3$ | $t-C_4H_9$ | |
| 67 | $CH_3$ | $SO_2CH_3$ | $CH_3$ | $CH_3$ | $t-C_4H_9$ | |
| 68 | $CH_3$ | $SO_2C_2H_5$ | $CH_3$ | $CH_3$ | $t-C_4H_9$ | |
| 69 | $CH_3$ | Cl | $C_2H_5$ | $CH_3$ | H | |
| 70 | $CH_3$ | $SO_2CH_3$ | $C_2H_5$ | $CH_3$ | H | |
| 71 | $CH_3$ | $SO_2CH_3$ | $i-C_3H_7$ | $CH_3$ | H | |
| 72 | $CH_3$ | $SO_2CH_3$ | $t-C_4H_9$ | $CH_3$ | H | |
| 73 | $C_2H_5$ | Cl | $CH_3$ | H | H | |
| 74 | $C_2H_5$ | $SO_2CH_3$ | $CH_3$ | H | H | |
| 75 | $C_2H_5$ | $SO_2C_2H_5$ | $CH_3$ | H | H | |
| 76 | $C_2H_5$ | Cl | $CH_3$ | H | $CH_3$ | |
| 77 | $C_2H_5$ | $SO_2CH_3$ | $CH_3$ | H | $CH_3$ | |
| 78 | $C_2H_5$ | $SO_2C_2H_5$ | $CH_3$ | H | $CH_3$ | |
| 79 | $C_2H_5$ | Cl | $CH_3$ | H | $C_2H_5$ | |
| 80 | $C_2H_5$ | $SO_2CH_3$ | $CH_3$ | H | $C_2H_5$ | |
| 81 | $C_2H_5$ | $SO_2C_2H_5$ | $CH_3$ | H | $C_2H_5$ | |
| 82 | $C_2H_5$ | Cl | $CH_3$ | H | $i-C_3H_7$ | |
| 83 | $C_2H_5$ | $SO_2CH_3$ | $CH_3$ | H | $i-C_3H_7$ | |
| 84 | $C_2H_5$ | $SO_2C_2H_5$ | $CH_3$ | H | $i-C_3H_7$ | |
| 85 | $C_2H_5$ | Cl | $CH_3$ | H | $t-C_4H_9$ | |
| 86 | $C_2H_5$ | $SO_2CH_3$ | $CH_3$ | H | $t-C_4H_9$ | |
| 87 | $C_2H_5$ | $SO_2C_2H_5$ | $CH_3$ | H | $t-C_4H_9$ | |
| 88 | $i-C_3H_7$ | Cl | H | H | H | |
| 89 | $i-C_3H_7$ | $SO_2CH_3$ | H | H | H | |
| 90 | $i-C_3H_7$ | Cl | $CH_3$ | H | H | |
| 91 | $i-C_3H_7$ | $SO_2CH_3$ | $CH_3$ | H | H | |
| 92 | $CH_3$ | $SCH_3$ | $CF_3$ | H | $CH_3$ | |
| 93 | $CH_3$ | $SOCH_3$ | $CF_3$ | H | $CH_3$ | |
| 94 | $CH_3$ | $SC_2H_5$ | $CF_3$ | H | $CH_3$ | |
| 95 | $CH_3$ | $SOC_2H_5$ | $CF_3$ | H | $CH_3$ | |
| 96 | $CH_3$ | Cl | $CF_3$ | H | $C_2H_5$ | |
| 97 | $CH_3$ | $SO_2CH_3$ | $CF_3$ | H | $C_2H_5$ | |

Reference Example 1

Preparation of methyl 4-methanesulfonyl-2-methyl-3-(3-metlyl-1,2-isoxazol-5-yl)benzoate

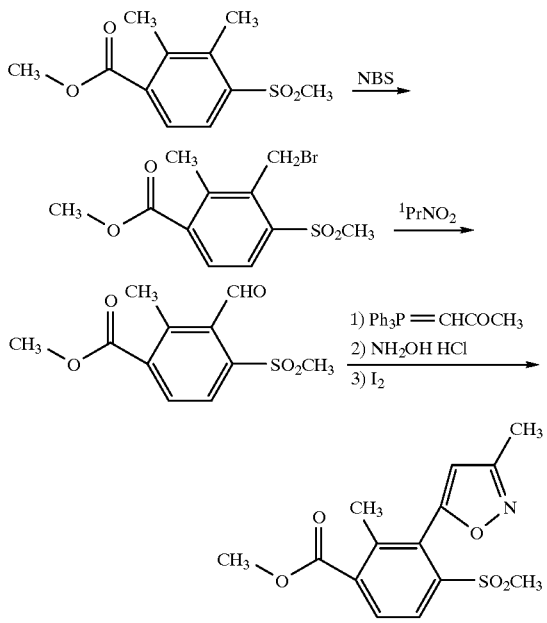

10.8 g (0.045 mol) of methyl 2,3-dimethyl-4-methanesulfonylbenzoate was dissolved in 80 ml of carbon tetrachloride, and 8.3 g (0.047 mol) of N-bromosuccinimide and 0.1 g of benzoyl peroxide were then added, followed by stirring for 3 hours under heating reflux. After the solution was allowed to cool, insoluble substance was removed by filtration, and the resulting filtrate was washed with an aqueous sodium hydrogen bisulfite solution, and then dried over anhydrous magnesium sulfate. Next, the solvent was distilled off under reduced pressure, the residue was purified through silica gel column chromatography to obtain 6.2 g of methyl 3-bromomethyl-4-methanesulfonyl-2-methylbenzoate in a state of crystals. Yield=43.4%.

2.6 g (0.014 mol) of a methanol solution containing 28% sodium methylate was added to 20 ml of methanol, and 1.3 g (0.015 mol) of 2-nitropropane was added dropwise at room temperature. Next, 4.4 g (0.014 mol) of methyl 3-bromomethyl-4-methanesu.lfonyl-2-methylbenzoate was added, and followed by stirring for 1 hour under heating reflux. After the solution was allowed to cool, 50 ml of 1N hydrochloric acid was added to the reaction solution, extraction was carried out with ethyl acetate. An ethyl acetate layer was washed with a saturated sodium chloride solution, and then dried over anhydrous magnesium sulfate. Next, the solvent was concentrated under reduced pressure to obtain 3.1 g of methyl 3-formyl-4-methanesulfonyl-2-methylbenzoate in the state of crystals. Yield=88%.

30 ml of benzene and then 3.85 g (0.012 mol) of 2-oxopropylidenetri phenylphospholane were added to 3.1 g (0.012 mol) of methyl 3-formyl-4-methanesulfonyl-2-methylbenzoate, followed by stirring for 1 hour under heating reflux. After the solution was allowed to cool, insoluble substance was removed by filtration, and the solvent was concentrated under reduced pressure to obtain methyl 4-methanesulfonyl-3-(3-oxo-1-butenyl)-2-methylbenzoate. Methyl 4-methanesulfonyl-3-(3-oxo-1-butenyl)-2-methylbenzoate thus obtained was dissolved in a solvent of 10 ml of ethanol and 10 ml of pyridine, and 1.1 g (0.016 mol) of hydroxyamine hydrochloride was added, followed by stirring for 1 hour under heating reflux. The resulting reaction mixture was poured into ice water, and extraction was carried out with ethyl acetate. Afterward, the resulting ethyl acetate layer was washed with 1N hydrochloric acid and subsequently with saturated sodium chloride solution, and then dried over anhydrous magnesium sulfate. Next, the solvent was distilled off under reduced pressure. The thus obtained methyl 4-methanesulfonyl-3-(3-hydroxyimino-1-butenyl)-2-methylbenzoate was dissolved in 15 ml of THF, and 15 ml of water containing 1.4 g (0.017 mol) of sodium hydrogencarbonate was added to the solution. Next, an aqueous solution obtained by dissolving 2.5 g (0.015 mol) of potassium iodide and 1.1 g (0.05 mol) of iodine in 12 ml of water was added, and the solution was heated under reflux for 3 hours under a condition that light was blocked. The reaction mixture was poured into ice water, and sodium hydrogen sulfite was then added, followed by extraction with ethyl acetate. The resulting organic layer was washed with a saturated sodium chloride solution, and then dried over anhydrous magnesium sulfate. Next, the solvent was distilled off under reduced pressure. The resulting residue was purified through silica gel column chromatography to obtain 0.84 g of methyl 4-methanesulfonyl-2-methyl-3-(3-methyl-1,2-isoxazol-5-yl)benzoate. Yield=23%.

$^1$H-NMR (CDCl$_3$, δppm); 2.36 (3H, s), 2.45 (3H, s), 2.92 (3H, s), 3.98 (3H, s), 6.41 (1H, s), 8.07 (1H, d), 8.16 (1H, d)

Reference Example 2

Preparation of methyl 4-methanesulfonyl-2-methyl-3-(3-methyl-1,2-isoxazol-5-yl)benzoate

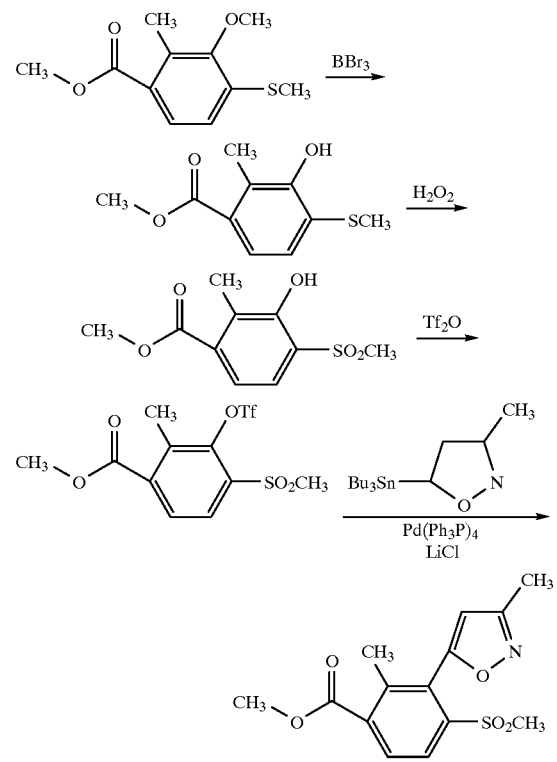

10 g (0.044 mol) of methyl 3-methoxy-2-methyl-4-methylthiobenzoate was dissloved in 90 ml of methylene chloride, and the solution was added dropwise to 90 ml of methylene chloride containing 8.4 ml (0.088 mol) of boron tribromide at 5 to 10° C. After stirring at room temperature for 4 hours, 50 ml of methanol was added dropwise under ice cooling, and the solution was then washed with water and next a saturated sodium chloride solution. After drying over anhydrous magnesium sulfate, the solvent was distilled off under reduced pressure to obtain 9.2 g of methyl 3-hydroxy-2-methyl-4-methylthiobenzoate. Yield=98%.

9.2 g (0.043 mol) of methyl 3-hydroxy-2-methyl-4-methylthiobenzoate was dissolved in 50 ml of acetic acid, and 14.8 g (0.130 mol) of 30% hydrogen peroxide was then added, followed by stirring at 80° C. for 3 hours. Next, the reaction mixture was poured into ice water, and precipitated crystals were collected by filtration, washed with water, and then dried to obtain 8.8 g of methyl 3-hydroxy-4-methanesulfonyl-2-methylbenzoate. Yield=83%.

8.8 g (0.036 mol) of methyl 3-hydroxy-4-methanesulfonyl-2-methyl-benzoate was dissolved in 100 ml of methylene chloride, and 8.3 g (0.11 mol) of pyridine was added. After the solution was cooled to 0° C., 12.2 g (0.043 mol) of anhydrous trifluoromethanesulfonic acid was added. After stirring at room temperature for 1 hour, the reaction mixture was washed with 1N hydrochloric acid and subsequently with saturated sodium chloride solution, and then dried over anhydrous magnesium sulfate. The solvent was distilled off under reduced pressure to obtain 13.5 g of methyl 4-methanesulfonyl-2-methyl-3-(trifluoromethanesulfonyl)oxybenzoate. Yield=99%.

1.65 g (4.4 mmol) of methyl 4-methanesulfonyl-2-methyl-3-(trifluoromethanesulfonyl)oxybenzoate and 1.97 g (5.3 mmol) of 3-methyl-5-(tributylstannyl)isoxazole were dissolved in 20 ml of dioxane, and 0.58 g (14 mmol) of lithium chloride, 0.1 g of tetrakis(triphenylphosph ine)-palladium-(0) and 0.01 g of 2,6-di-t-butyl-4-methyl phenol were then added, followed by stirring at 140° C. for 3 hours in an autoclave. After the solution was allowed to cool, insoluble substance was removed by filtration, and the solvent was distilled off under reduced pressure. Afterward, the solution was purified by using a silica gel column chromatography to obtain 0.74 g of methyl 4-methanesulfonyl-2-methyl-3-(3-methyl-1,2-isoxazol-5-yl)benzoate. Yield=55%.

Reference Example 3

Preparation of 4-methanesulfonyl-2-methyl-3-(3-methyl-1,2-isoxazol-5-yl) benzoic acid

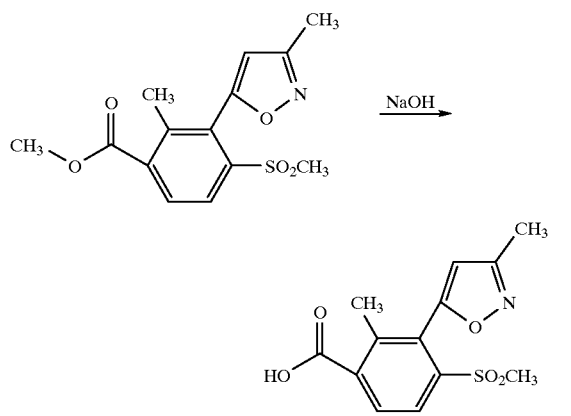

3.11 g (10.1 mmol) of methyl 4-methanesulfonyl-2-methyl-3-(3-methyl-1,2-isoxazol-5-yl)benzoate was dissolved in 30 ml of methyl alcohol, and 30 ml of a 1N aqueous caustic soda solution was then added, followed by stirring at room temperature overnight. The resulting reaction mixture was poured into ice water, and then acidified with concentrated hydrochloric acid. Next, the precipitated crystals were collected by filtration, washed with water, and then dried to obtain 2.85 g of 4-methanesulfonyl-2-methyl-3-(3-methyl-1,2-isoxazol-5-yl)benzoic acid. Yield=96% and m.p.=242 to 244° C.

Preparation of Compounds to be Used for Comparison

A compound A for comparison purpose is described in WO 93/17083 Gazette, and compounds B and C are the compounds described in WO 96/26206 Gazette. Also, a compound D is the one given as an example in WO 96/26206 Gazette. The compound D was prepared according to the same method as described in the Example 1 by using 4-methanesulfonyl-2-methyl-3-(3-methyl-1,2-isoxazol-5-yl)benzoic acid, which is prepared in Reference Example 3, and 1,3-dimethyl-5-hydroxypyrazole as a starting raw material. m.p. 137–139° C.

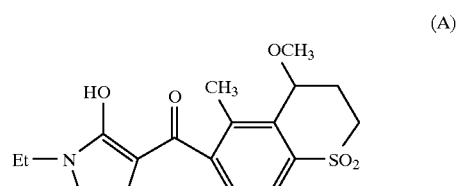

(A)

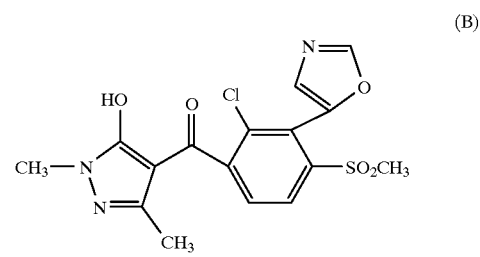

(B)

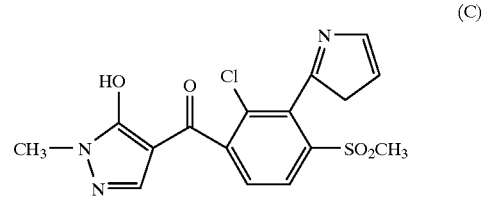

(C)

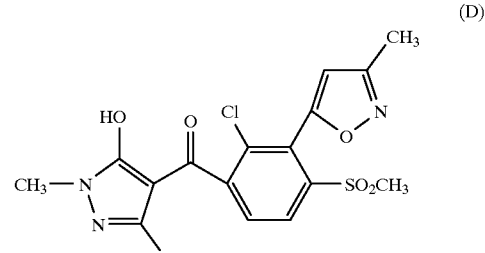

(D)

Advantageous Effect of the Invention

The compounds of the present invention can provide a high herbicidal activity even in both application manners including soil treatment and foliar application under upland crop farming condition, and they are effective for various kinds of hazardous weeds, such as giant foxtail, cocklebur, pigweed and wild oat. These compounds of the present invention include compounds which are selectively non-toxic to crops, such as corn, wheat, barley, soybean and cotton.

Furthermore, the compounds of the present invention include compounds which can give a plant growth regulating activity, such as a growth retardant action, to useful plants such as agricultural crops, ornamental flowers, fruit trees, etc.

In addition, the compounds of the present invention particularly have the excellent herbicidal effect on weeds, such as barnyard grass, *Cyperus difformis, Sagittaria trifolia* and *Scirpus juncoides*, and have a selectivity to rice plants.

Moreover, the compounds of the present invention can be applied to the prevention of weeds in orchard fields, lawns, railway passages, vacant lands and the like.

Herbicide

The herbicidal composition according to the present invention contains one or more compounds of the present invention as the active components. When actually applied, the compound of the present invention can be used in a pure form without adding any other components, and for the purpose of using the compounds of the present invention as a plant protection chemical, the compounds of the present invention can be used in a form of formulation customarily employed for plant protection chemicals, i.e., wettable powders, granules, powders, emulsifiable concentrates, water soluble powders, suspension or flowable formulations. As an additive and a carrier which can be used in the case that a solid agent is intended, plant-oriented powders, such as soybean powder and wheat powder, mineral fine powders such as diatomaceous earth, apatite, gypsum, talc, bentonite, pyrophylite and clay, and organic and inorganic compounds such as sodium benzoate, urea and Glauber's salt, can be used. In the case that a liquid-type formulation is intended, a solvent, for examples, petroleum fractions such as kerosine, xylene and solvent naphtha, cyclohexane, cyclohexanone, dimethylformamide, dimethyl sulfoxide, alcohols, acetone, trichloroethylene, methyl isobutyl ketone, mineral oils, vegetable oils and water can be used. In order to secure the formulation to uniform and stable condition, a surface active agent can be added, if necessary.

The concentration of the active component in the herbicidal composition of the present invention depends upon the form of the above-mentioned agent, but for example, in the case of the wettable powder, it is in the range of 5 to 90%. preferably 10 to 85%; in the case of the emulsion, it is in the range of 3 to 70%, preferably 5 to 60%; and in the case of the granules, it is in the range of 0.01 to 50%, preferably 0.05 to 40%.

The wettable powder or emulsion thus obtained is respectively diluted to a predetermined concentration with water to obtain a suspension or an emulsion, and the granules can be directly sprinkled on or mixed with a soil before or after. the germination of the weeds. In fact, when the herbicide of the present invention is applied, a suitable amount of the active component to be applied is 0.1 g or more per hectare.

Furthermore, the herbicide of the present invention can be used by mixing with any of known fungicides, insecticides, acaricides, other herbicides, plant growth regulators and fertilizers. In particular, when the herbicide of the present invention is mixed with the other herbicides, the amount of the herbicide of the present invention can be reduced. In addition, the employment of the herbicide of the present invention leads to the reduction of labor, and higher effects of the present invention by the synergistic effect of the mixed agents can also be expected. In this case, it is also possible to combine the herbicide of the present invention with a plurality of the known herbicides.

Examples of the agents which can suitably be mixed with the herbicide of the present invention include anilide-containing herbicides, such as diflufenican and propanil, chloroacetanilide-containing herbicides, such as alachlor and pretilachlor, aryloxyalkanic acid-containing herbicides, such as 2,4-D and 2,4-DB, aryloxyphenoxyalkanic acid-containing herbicides, such as diclofop-methyl and fenoxapropethyl, arylcarboxylic acid-contaning herbicides, such as dicamba and pyrithiobac-sodium, imidazolinone-containing herbicides, such as imazaquin and imazethapyr, urea-containing herbicides, such as diuron and isoproturon, carbamate-containing herbicides, such as chlorpropham and phenmedipham, thiocarbamate-containing herbicides, such as thiobencarb and EPTC, dinitroaniline-containing herbicides, such as trifluralin and pendimethalin, diphenyl ether-containing herbicides, such as acifluorfen-sodium and fomesafen, sulfonylurea-containing herbicides, such as bensulfuron-methyl and nicosulfuron, triazinone-containing herbicides, such as metribuzin and metamitron, triazine-containing herbicides, such as atrazine and cyanazine, triazopyrimidine-containing herbicides such as flumetsulam, nitrile-containing herbicides, such as bromoxynil and dichlobenil, pyridazinone-containing herbicides, such as chloridazon and norflurazon, phosphoric acid-containing herbicides, such as glyphosate and glufosinate, quaternary ammonium salt-containing herbicides, such as paraquat and difenzoquat, cyclic imide-containing herbicides, such as flumiclorac-pentyl and fluthiacet-methyl, other herbicides, such as isoxaben, ethofumesate, oxadiazon, quinclorac, clomazone, sulcotrione, cinmethylin, dithiopyr, pyrazolate, pyridate, flupoxam, bentazone and benfuresate, and cyclohexanedione-containing herbicides, such as sethoxydim and tralkoxydim. Moreover, to a combination of these active components, a vegetable oil or an oil condensate can be added.

EXAMPLES

Herbicide

Now, some formulation examples for the herbicidal composition according to the present invention are described hereinbelow, however, the active component compounds, additives and the addition ratio should not limited to the scope described in these examples and those can be altered or expanded in a wide range. In the formulation examples, "part(s)" means "part(s) by weight".

Example 2

Wettable powder formulation

| Compound of the present invention | 20 parts |
|---|---|
| White carbon | 20 parts |
| Diatomaceous earth | 52 parts |
| Sodium alkylsulfate | 8 parts |

These materials were uniformly mixed, and then finely ground to obtain a wettable powder containing 20% of the effective component.

Example 3

Emulsifiable Concentrate Formulation

| | |
|---|---|
| Compound of the present invention | 20 parts |
| Xylene | 55 parts |
| Dimethylformamide | 15 parts |
| Polyoxyethylene phenyl ether | 10 parts |

These materials were uniformly mixed and dissolved to obtain an emulsion containing 20% of the effective component.

Example 4

Granular Formulation

| | |
|---|---|
| Compound of the present invention | 5 parts |
| Talc | 40 parts |
| Clay | 38 parts |
| Bentonite | 10 parts |
| Sodium alkylsulfate | 7 parts |

These materials were uniformly mixed, finely ground, and then granulated to obtain granules having a diameter of 0.5 to 1.0 mm and containing 5% of the effective component.

Test Examples

Now, test examples regarding the herbicidal effect of the herbicide according to the present invention are described hereinbelow.

The herbicidal effect was evaluated in accordance with the following evaluation criteria, and it is represented by each index expressing the strength of a herbicidal composition.

Evaluation Criteria

| Weed killed in % | Herbicidal Index |
|---|---|
| 0% | 0 |
| 20–29% | 2 |
| 40–49% | 4 |
| 60–69% | 6 |
| 80–89% | 8 |
| 100% | 10 |

Furthermore, values of 1, 3, 5, 7 and 9 mean values between 0 and 2, 2 and 4, 4 and 6, 6 and 8, and 8 to 10, respectively.

$$\% \text{ of killed weeds} = \frac{(\text{Fresh weight of shoots in non-treated plot} - \text{Fresh weight of shoots in a treated plot})}{\text{Fresh weight of shoots in non-treated plot}} \times 100$$

Test Example 1

Foliar Application to Weeds Grown in Upland Crop Fields

Pots in a size of 200 cm$^2$ were filled with a soil, and seeds of velvet leaf, pigweed, cocklebur, giant foxtail and corn were planted in the pots, respectively. After the seeds were covered with the soil, they were allowed to grow in a greenhouse. When the respective plants grew up to a height of 5 to 25 cm, aqueous dilute solutions of the emulsion shown in Example 3 containing sample compounds were sprayed on stems and leaves of the weeds by using a small sprayer so that each active component in an amount of 250 g/ha was applied into each pots. After 3 weeks, the herbicidal effects of the respective compounds to the weeds were inspected, and the results are shown in Table 2.

It is shown that the compounds according to the present invention provide excellent herbicidal activity against various types of weeds, and, in particular, are having an high selectivity to maize plants which does not give harmful effect thereon.

TABLE 2

| Compound No. | Velvet leaf | Pigweed | Cocklebur | Giant Foxtail | Maize |
|---|---|---|---|---|---|
| 20 | 10 | 10 | 10 | 10 | 0 |
| 23 | 10 | 10 | 10 | 10 | 0 |
| A | 6 | 8 | 10 | 9 | 2 |
| B | 7 | 2 | 10 | 6 | 0 |
| C | 10 | 7 | 10 | 10 | 4 |
| D | 10 | 10 | 9 | 10 | 7 |

Possible Industrial Use

As described above, a compound of formula [I] has an excellent selectivity in its herbicidal activity to crops and weeds, and particularly, it is selectively safe to maize plants. Therefore, a herbicidal composition comprising the compound according to the present invention can be useful as a selective herbicide for weed control in maize fields.

What is claimed is:

1. A comund of formula [I];

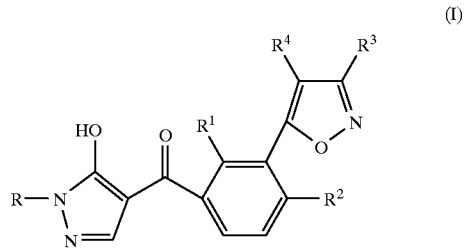

or a salt thereof in which R$^1$ is a C$_{1-6}$ alkyl group, R$^2$ is a halogen atom, a C$_{1-6}$ alkylthio group, a C$_{1-6}$ alkylsulfinyl group or a C$_{1-6}$ alkylsulfonyl group, R$^3$ and R$^4$ are each independently hydrogen, a C$_{1-6}$ alkyl group or a C$_{1-6}$ haloalkyl group, and R is hydrogen or a C$_{1-6}$ alkyl group.

2. A compound according to claim 1, in which R$^1$ and R$^3$ are methyl, R$^2$ is chlorine or methylsulfonyl, R$^4$ is hydrogen, and R is methyl or ethyl.

3. A herbicidal composition, characterized in that it contains as active gent one or more compounds of formula [I];

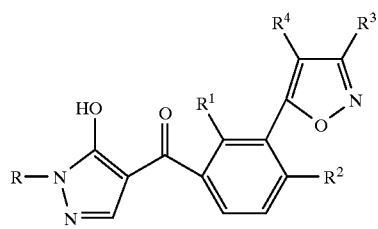

(I)

or salts thereof in which $R^1$ is a $C_{1-6}$ alkyl group, $R^2$ is a halogen atom, a $C_{1-6}$ alkylthio group, a $C_{1-6}$ alkylsulfinyl group or a $C_{1-6}$ alkylsulfonyl group, $R^3$ and $R^4$ are each independently hydrogen, a $C_{1-6}$ alkyl group or a $C_{1-6}$ haloalkyl group, and R is hydrogen or a $C_{1-6}$ alkyl group.

4. A herbicidal composition according to claim 3, in which $R^1$ and $R^3$ are methyl, $R^2$ is chlorine or methylsulfonyl, $R^4$ is hydrogen, and R is methyl or ethyl.

* * * * *

UNITED STATES PATENT AND TRADEMARK OFFICE
CERTIFICATE OF CORRECTION

PATENT NO. : 5,939,360
DATED : August 17, 1999
INVENTOR(S) : Hiroyuki Adachi et al.

It is certified that error appears in the above-indentified patent and that said Letters Patent is hereby corrected as shown below:

On title page, [57] ABSTRACT replace "in which $R_1$ is"

with -- in which $R^1$ is--

On title page, [57] ABSTRACT after "$R^1$, $R^2$, $R^3$, $R^4$"

add --and R--

In the text, col. 24, last line replace "gent"

with --agent--

Signed and Sealed this

Twenty-third Day of November, 1999

Attest:

Q. TODD DICKINSON

*Attesting Officer*     *Acting Commissioner of Patents and Trademarks*